(12) United States Patent
Hahn et al.

(10) Patent No.: US 10,626,157 B2
(45) Date of Patent: Apr. 21, 2020

(54) SFRP5-DERIVED PEPTIDE FRAGMENT AND COSMETIC COMPOSITION FOR SKIN WHITENING CONTAINING SAME

(71) Applicants: KNU-INDUSTRY COOPERATION FOUNDATION, Chuncheon-si, Gangwon-do (KR); SUPADELIXIR INC., Chuncheon-si, Gangwon-do (KR)

(72) Inventors: Jang-Hee Hahn, Chuncheon-si (KR); Dong-Young Lim, Gwangju-si (KR)

(73) Assignees: KNU-INDUSTRY COOPERATION FOUNDATION, Chuncheon-si (KR); SUPADELIXIR INC., Chuncheon-si (KR)

( * ) Notice: Subject to any disclaimer, the term of this patent is extended or adjusted under 35 U.S.C. 154(b) by 0 days.

(21) Appl. No.: 15/664,277

(22) Filed: Jul. 31, 2017

(65) Prior Publication Data

US 2017/0334965 A1    Nov. 23, 2017

Related U.S. Application Data

(62) Division of application No. 15/122,833, filed as application No. PCT/KR2015/012571 on Nov. 23, 2015, now Pat. No. 9,868,775.

(30) Foreign Application Priority Data

Nov. 24, 2014    (KR) .................. 10-2014-0164481

(51) Int. Cl.
| | |
|---|---|
| *C07K 14/705* | (2006.01) |
| *A61K 8/64* | (2006.01) |
| *C07K 5/083* | (2006.01) |
| *C07K 5/103* | (2006.01) |
| *C07K 5/11* | (2006.01) |
| *A61Q 19/02* | (2006.01) |
| *C07K 7/06* | (2006.01) |
| *A61K 8/66* | (2006.01) |
| *G01N 33/53* | (2006.01) |

(52) U.S. Cl.
CPC .............. *C07K 14/705* (2013.01); *A61K 8/64* (2013.01); *A61K 8/66* (2013.01); *A61Q 19/02* (2013.01); *C07K 5/0806* (2013.01); *C07K 5/0808* (2013.01); *C07K 5/101* (2013.01); *C07K 5/1013* (2013.01); *C07K 5/1019* (2013.01); *C07K 7/06* (2013.01); *G01N 33/53* (2013.01); *A61K 2800/782* (2013.01)

(58) Field of Classification Search
CPC .... A61K 38/07; C07K 5/0806; C07K 5/0808; C07K 5/101; C07K 5/1013; C07K 5/1019
See application file for complete search history.

(56) References Cited

U.S. PATENT DOCUMENTS

| | | | |
|---|---|---|---|
| 9,067,987 B2 * | 6/2015 | Galeotti | ............... A61K 39/095 |
| 2006/0003322 A1 * | 1/2006 | Bentwich | ............... G16B 20/00 |
| | | | 435/6.16 |

FOREIGN PATENT DOCUMENTS

| | | | | |
|---|---|---|---|---|
| EP | 2 428 116 A1 | 3/2012 | | |
| WO | 2004/002418 A2 | 1/2004 | | |
| WO | WO-2007117444 A2 * | 10/2007 | ........... | C12N 15/111 |
| WO | 2008/031009 A2 | 3/2008 | | |

OTHER PUBLICATIONS

Yin et al., Wnt Signaling in Zebrafish Swimbladder Development, www.plosone.org, Mar. 2011, vol. 6, Issue 3, e18431. (Year: 2011).*
*Homo sapiens* secreted frizzled-related protein 5, GenBank: BC050435.1, Aug. 11, 2006, accessed on Sep. 16, 2019, available online at https://www.ncbi.nlm.nih.gov/nuccore/BC050435.1. (Year: 2006).*
Definition of Reagent, available online at https://www.merriam-webster.com/dictionary/reagent, accessed on Sep. 16, 2019. (Year: 2019).*
Laeremans et al., "Blocking of Frizzled Signaling With a Homologous Peptide Fragment of Wnt3a/Wnt5a Reduces Infarct Expansion and Prevents the Development of Heart Failure After Myocardial Infarction", Circulation, 2011, 124: 1626-1635.
Wu et al., "Structural Requirements of Angiotensin I-Converting Enzyme Inhibitory Peptides: Quantitative Structure-Activity Relationship Study of Di- and Tripeptides", J. Agric. Food Chem., 2006, 54, 732-738.

* cited by examiner

*Primary Examiner* — James H Alstrum-Acevedo
*Assistant Examiner* — Kaipeen E Yang
(74) *Attorney, Agent, or Firm* — Vorys, Sater, Seymour & Pease LLP; Mih Suhn Koh (57) ABSTRACT

Provided is a peptide fragment derived from secreted frizzled protein 5 (Sfrp5), i.e., a peptide fragment selected from the group consisting of the peptides as set forth in SEQ ID NOs: 1 to 9 and a cosmetic composition for skin-whitening and/or inhibiting skin pigmentation comprising the same as an active ingredient. The peptide fragment inhibits melanin formation in melanocytes, thereby having an inhibitory activity against skin pigmentation. Further provided is a reagent for researching or analyzing the inhibition of Wnt signaling pathways comprising the peptide fragment.

2 Claims, 6 Drawing Sheets

Specification includes a Sequence Listing.

SEQUENCE LISTING

<160> NUMBER OF SEQ ID NOS: 19

<210> SEQ ID NO 1
<211> LENGTH: 6
<212> TYPE: PRT
<213> ORGANISM: Artificial Sequence
<220> FEATURE:
<223> OTHER INFORMATION: Peptide fragment

<400> SEQUENCE: 1

Lys Ile Gly Ala Gln Lys
1               5

<210> SEQ ID NO 2
<211> LENGTH: 4
<212> TYPE: PRT
<213> ORGANISM: Artificial Sequence
<220> FEATURE:
<223> OTHER INFORMATION: Peptide fragment

```
<400> SEQUENCE: 2

Lys Ile Gly Ala
1

<210> SEQ ID NO 3
<211> LENGTH: 4
<212> TYPE: PRT
<213> ORGANISM: Artificial Sequence
<220> FEATURE:
<223> OTHER INFORMATION: Peptide fragment

<400> SEQUENCE: 3

Ile Gly Ala Gln
1

<210> SEQ ID NO 4
<211> LENGTH: 4
<212> TYPE: PRT
<213> ORGANISM: Artificial Sequence
<220> FEATURE:
<223> OTHER INFORMATION: Peptide fragment

<400> SEQUENCE: 4

Gly Ala Gln Lys
1

<210> SEQ ID NO 5
<211> LENGTH: 3
<212> TYPE: PRT
<213> ORGANISM: Artificial Sequence
<220> FEATURE:
<223> OTHER INFORMATION: Petide fragment

<400> SEQUENCE: 5

Lys Ile Gly
1

<210> SEQ ID NO 6
<211> LENGTH: 3
<212> TYPE: PRT
<213> ORGANISM: Artificial Sequence
<220> FEATURE:
<223> OTHER INFORMATION: Petide fragment

<400> SEQUENCE: 6

Ile Gly Ala
1

<210> SEQ ID NO 7
<211> LENGTH: 3
<212> TYPE: PRT
<213> ORGANISM: Artificial Sequence
<220> FEATURE:
<223> OTHER INFORMATION: Petide fragment

<400> SEQUENCE: 7

Gly Ala Gln
1

<210> SEQ ID NO 8
<211> LENGTH: 3
<212> TYPE: PRT
<213> ORGANISM: Artificial Sequence
<220> FEATURE:
<223> OTHER INFORMATION: Petide fragment

<400> SEQUENCE: 8
```

Ala Gln Lys
1

<210> SEQ ID NO 9
<211> LENGTH: 4
<212> TYPE: PRT
<213> ORGANISM: Artificial Sequence
<220> FEATURE:
<223> OTHER INFORMATION: Peptide fragment

<400> SEQUENCE: 9

Cys Glu Ala Val
1

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ctcgagctca tggactttcc                                              20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ccagttccga ggttgttgtt                                              20

<210> SEQ ID NO 12
<211> LENGTH: 17
<212> TYPE: DNA
<213> ORGANISM: Artificial Sequence
<220> FEATURE:
<223> OTHER INFORMATION: Primer

<400> SEQUENCE: 12
atccagaagc tgacagg                                                 17

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
tttgagaggc atccgcta                                                18

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
agcagtagtt ggcgctttgt                                              20

<210> SEQ ID NO 15

```
<211> LENGTH: 20
<212> TYPE: DNA
<213> ORGANISM: Artificial Sequence
<220> FEATURE:
<223> OTHER INFORMATION: Primer

<400> SEQUENCE: 15
tcaaccaggt ggttttgtga                                               20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tgccacaaca tggatgaact                                               20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
ttgtgcccac caaacagtaa                                               20

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
gcaaattcca tggcaccgt                                                19

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
ccaaaatcaa gtggggcga                                                19
```

SFRP5-DERIVED PEPTIDE FRAGMENT AND COSMETIC COMPOSITION FOR SKIN WHITENING CONTAINING SAME

TECHNICAL FIELD

The present invention relates to peptide fragments derived from Secreted frizzled protein 5 (Sfrp5) and a cosmetic composition for skin-whitening and/or for inhibiting skin pigmentation comprising the same as an active ingredient. And also, the present invention relates to a reagent for researching or analyzing the inhibition of Wnt signaling to pathways comprising the peptide fragment.

BACKGROUND ART

Melanin is dark brown pigments found in the eyes or on the skin, hair, etc. and plays positive roles in protecting the body or maintaining the body temperature, through blocking the penetration of ultraviolet radiation in a way that it absorbs the ultraviolet radiation over a certain amount. However, excessive exposure to ultraviolet radiation leads to oversecretion of melanin for blocking the skin penetration thereof, which often causes skin color changes. It is known that melanin is produced by the concurrence of melanin-producing enzymes (e.g., tyrosinase) and hormones.

Melanoma is a tumor formed by malignant alteration of melanin-producing cells (i.e., melanocytes). Although melanoma can occur in any body parts where melanocytes are present, the incidence thereof is the highest in the skin. And also, it is known that its malignancy is significantly high among various skin tumors. Although the incidence of melanoma is relatively low in the East in comparison with in the West, it is increasing year by year, showing the tendency that it begins to increase from twenty-year-old; and then rapidly increases in more than forty-year-old. It is thought that melanoma results mainly from genetic causes and/or exposure to ultraviolet radiation.

Meanwhile, Wnt is known as a cell signaling molecule secreted from various body cells, which is involved in three kinds of pathways, i.e., canonical Wnt pathway, non-canonical planar cell polarity pathway, and non-canonical Wnt/calcium pathway. Under normal conditions, Wnt is bound with Wnt antagonists such as Wnt inhibitory factor (WIF) and thus cannot be involved in the signaling. However, under certain circumstances in which Wnt antagonists such as WIF cannot be expressed, Wnt is bound with the receptor, i.e., Frizzled, to generate the signaling. Secreted frizzled protein 5 (Sfrp5) is a secretory protein, which is known as one of the Wnt antagonists, similar to WIF. Sfrp5 contains the site having homology with the Wnt-binding site in Frizzled and thus controls the binding between Wnt and Frizzled proteins. The binding of Wnt with the receptor (Frizzled) in melanocytes leads to the β-catenin activation, thereby promoting the expression of MITF to control the melanin biosynthesis. Therefore, it is expected that the control of Wnt signaling pathways inhibits the expression of MITF, thereby being able to decrease pigmentation.

DISCLOSURE

Technical Problem

The present inventors have designed various peptide fragments derived from Sfrp5, which inhibit the binding between Wnt and Frizzled, through binding with Wnt; and evaluated the activities thereof. Surprisingly, the present inventors have found that the Sfrp5-derived specific peptide fragments inhibit Wnt signaling pathways, thereby exhibiting inhibitory activities against melanin production and skin pigmentation in skin cells.

Therefore, it is an object of the present invention to provide the Sfrp5-derived specific peptide fragments.

It is another object of the present invention to provide a cosmetic composition for skin-whitening and/or for inhibiting skin pigmentation, comprising the Sfrp5-derived specific peptide fragments as an active ingredient.

It is still another object of the present invention to provide a reagent for researching or analyzing the inhibition of Wnt signaling pathways, comprising the Sfrp5-derived specific peptide fragments.

Technical Solution

In accordance with an aspect of the present invention, there is provided a secreted frizzled protein 5 (Sfrp5)-derived peptide fragment selected from the group consisting of the peptides as set forth in SEQ ID NOs: 1 to 9.

In accordance with another aspect of the present invention, there is provided a cosmetic composition for skin-whitening, comprising a secreted frizzled protein 5 (Sfrp5)-derived peptide fragment selected from the group consisting of the peptides as set forth in SEQ ID NOs: 1 to 9 as an active ingredient.

In an embodiment, the cosmetic composition of the present invention may be a cosmetic composition for inhibiting skin pigmentation, comprising a secreted frizzled protein 5 (Sfrp5)-derived peptide fragment selected from the group consisting of the peptides as set forth in SEQ ID NOs: 1 to 9 as an active ingredient. The skin pigmentation may be a skin pigmentation induced by exposure to ultraviolet radiation.

In accordance with still another aspect of the present invention, there is provided a reagent for researching or analyzing the inhibition of Wnt signaling pathways, comprising a secreted frizzled protein 5 (Sfrp5)-derived peptide fragment selected from the group consisting of the peptides as set forth in SEQ ID NOs: 1 to 9.

Advantageous Effects

It has been found by the present invention that the secreted frizzled protein 5 (Sfrp5)-derived specific peptide fragments, i.e., the peptides as set forth in SEQ ID NOs: 1 to 9, inhibit the melanin production in melanocytes, exhibiting a skin-whitening activity and/or an inhibitory activity against skin pigmentation. Therefore, the peptide fragments can be usefully applied to a cosmetic composition for skin-whitening, especially for inhibiting skin pigmentation. And also, the peptide fragments can be usefully used as a research or analytical reagent, i.e., as an inhibitor against Wnt signaling pathways, in the biological and/or medical fields.

BEST MODE

The present invention provides a secreted frizzled protein 5 (Sfrp5)-derived peptide fragment selected from the group consisting of the peptides as set forth in SEQ ID NOs: 1 to 9. And also, the present invention provides a cosmetic composition for skin-whitening, comprising a secreted frizzled protein 5 (Sfrp5)-derived peptide fragment selected from the group consisting of the peptides as set forth in SEQ ID NOs: 1 to 9 as an active ingredient.

It has been found by the present invention that the secreted frizzled protein 5 (Sfrp5)-derived peptide fragments, i.e., the peptides as set forth in SEQ ID NOs: 1 to 9, inhibit the melanin production in melanocytes, exhibiting an inhibitory activity against epidermal skin pigmentation. Therefore, the peptide fragments can be usefully applied to a cosmetic composition for skin-whitening, especially for inhibiting skin pigmentation.

In an embodiment, the cosmetic composition of the present invention may be a cosmetic composition for inhibiting skin pigmentation, comprising a secreted frizzled protein 5 (Sfrp5)-derived peptide fragment selected from the group consisting of the peptides as set forth in SEQ ID NOs: 1 to 9 as an active ingredient. The term "skin pigmentation" refers to excessive pigment accumulation in skin keratinocytes resulting from internal and external causes; and includes preferably a skin pigmentation induced by exposure to ultraviolet radiation.

The cosmetic composition of the present invention may be prepared in various forms according to conventional methods thereof. For example, the cosmetic composition may be prepared in forms of cosmetic products, cosmetic solutions, creams, lotions, etc., which may be diluted with a cleansing water, an astringent solution, or a moisture solution, for the use thereof. And also, the cosmetic composition may include conventional excipients, such as a stabilizer, a solubilizing agent, vitamins, a pigment, a flavoring agent, which are conventionally used in the field of cosmetic composition. In the cosmetic composition, the peptide fragment may be present in an amount enough to provide the skin-whitening effects or the inhibitory effects against skin pigmentation, for example in an amount ranging from 0.001 to 10 weight %, preferably about 0.01 to 1 weight %, based on the total weight of the composition.

The present invention also provide a reagent for researching or analyzing the inhibition of Wnt signaling pathways, comprising a secreted frizzled protein 5 (Sfrp5)-derived peptide fragment selected from the group consisting of the peptides as set forth in SEQ ID NOs: 1 to 9. The reagent of the present invention can be usefully used as a research or analytical reagent in various research fields, e.g., in the biological and/or medical fields. The research or analytical reagent may be in a form of the peptide fragment per se or in a form solubilized or dispersed in an appropriate carrier, e.g., phosphate buffered saline (PBS).

Hereinafter, the present invention will be described more specifically by the following examples and experimental examples. However, the following examples and experimental examples are provided only for illustrations and thus the present invention is not limited to or by them.

Example 1: Synthesis of Peptide Fragments

The peptide fragments of SEQ ID NOs: 1 to 9 were synthesized with an automatic peptide synthesizer (PeptrEx-R48, Peptron, Daejeon, Korea) using a FMOC solid-phase method. The synthesized peptide fragments were purified and analyzed by reverse-phase high-performance liquid chromatography (reverse-phase HPLC) (Prominence LC-20AB, Shimadzu, Japan) using a C18 analytical RP column (Shiseido capcell pak), and identified using a mass spectrometer (HP 1100 Series LC/MSD, Hewlett-Packard, Roseville, U.S.A.).

TABLE 1

| Peptide name | SEQ ID NO | Amino acid sequence |
|---|---|---|
| SE215A | SEQ ID NO: 1 | Lys-Ile-Gly-Ala-Gln-Lys |
| SE215B | SEQ ID NO: 2 | Lys-Ile-Gly-Ala |
| SE215C | SEQ ID NO: 3 | Ile-Gly-Ala-Gln |
| SE215D | SEQ ID NO: 4 | Gly-Ala-Gln-Lys |
| SE215E | SEQ ID NO: 5 | Lys-Ile-Gly |
| SE215F | SEQ ID NO: 6 | Ile-Gly-Ala |
| SE215G | SEQ ID NO: 7 | Gly-Ala-Gln |
| SE215H | SEQ ID NO: 8 | Ala-Gln-Lys |
| SE215I | SEQ ID NO: 9 | Cys-Glu-Ala-Val |

Example 2: Preparation of the Compositions Containing Peptide Fragments

The peptide fragments of SEQ ID NOs: 1 to 9 were respectively dissolved in phosphate buffered saline (PBS) to a concentration of 1 M. The resultant protein solutions were also used in the following experimental examples.

Experimental Example 1: Evaluation of the Effects of the Peptide Fragments of the Present Invention on Bindings Between CREB or MITF and β-Catenin in the Mouse Melanoma Cell Line B16F1

The effects of the peptide fragments of the present invention on the β-catenin activation, which plays a critical role in Wnt signaling pathways, were evaluated using an in situ proximity ligation assay. The evaluation was performed with a commercially available kit, i.e., DUOLINK II in situ kit from Olink Bioscience, Sweden.

Figure 1A:
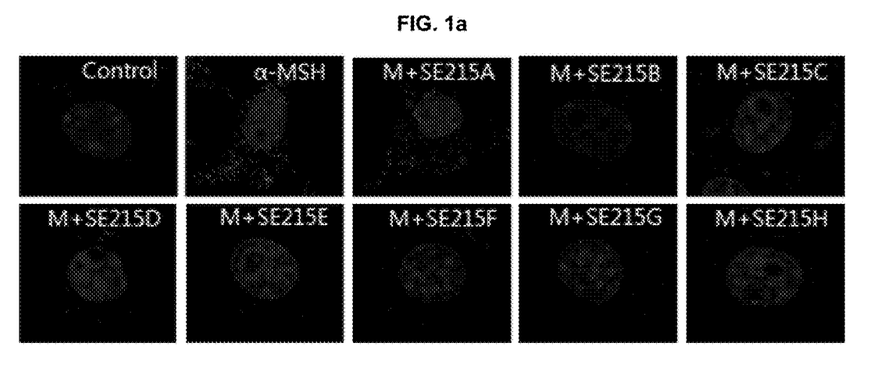
FIGS. 1a to 1c show the results obtained by evaluating the effects of the peptides of the present invention on the bindings between MITF or CREB and β-catenin in the mouse melanoma cell line.
Figure 1B:
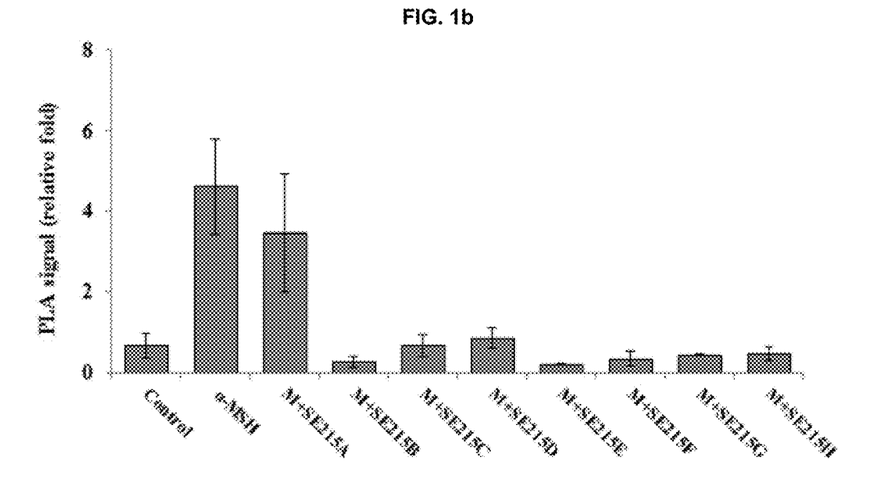

The mouse melanoma cell line B16F1 cells (Korean Cell Line Bank, Seoul) were added to 1 ml of DMEM in each well of a 24-well plate ($5 \times 10^4$ cells per well), each well having a 12 mm glass in the bottom thereof. The cells were then stabilized through incubating in a 5% $CO_2$ incubator at 37° C. for 24 hours. α-MSH (Sigma Co, MO, USA), a melanocyte-stimulating hormone (0.1 μM), and the peptide fragments of the present invention (1 μM) were treated to each well. The cells were cultured in a 5% $CO_2$ incubator at 37° C. for 24 hours and then fixed with 4% paraformaldehyde. After a drop of the blocking solution was added to the cells on the 12 mm glass, the cells were then incubated at 37° C. for 30 minutes. Activation of the Wnt receptor increases the interaction between CREB (cyclic AMP response element-binding) and β-catenin. For determining the interaction levels thereof, the cells were treated with an anti-CREB polyclonal antibody (Santa Cruz Co., CA, USA) and an anti-β-catenin mouse monoclonal antibody (Santa Cruz Co., CA, USA) at 37° C. After incubating 30 minutes therefrom, the cells were treated with the PLA probe solution at 37° C. for 1 hour, with the ligation solution for 30 minutes, and then with the amplification solution for 100 minutes. After washing the cells with the washing buffer, the number of the red spots was measured with a confocal microscopy. The results thereof are shown in FIGS. 1a and 1b. In FIGS. 1a and 1b, the control means the group of no treatment and the α-MSH means the group treated with only α-MSH (i.e., without peptide treatment).

As shown in FIGS. 1a and 1 b, the bindings between CREB and β-catenin were significantly decreased by the peptides of SEQ ID NOs: 1 to 8. These results show that the peptide fragments of the present invention effectively inhibit the β-catenin activation in melanocytes, thereby inhibiting the Wnt signaling pathways.

Figure 1C:
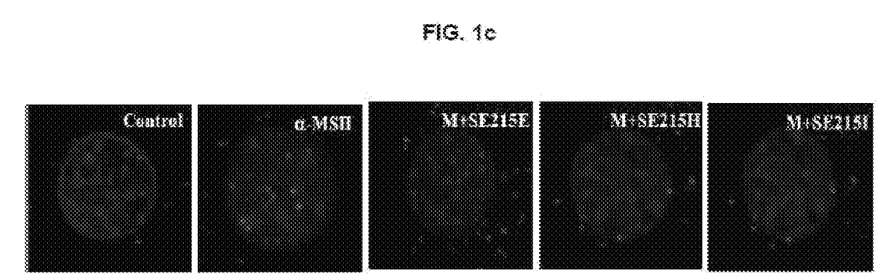

And also, according to similar methods in the above, we investigated the inhibitory effects of the peptides of SEQ ID NOs: 5, 8, and 9 on the binding between MITF and β-catenin. The bindings between MITF and β-catenin were significantly decreased by the treatment of these peptides (see FIG. 1c). These results also show that the peptide fragments of the present invention effectively inhibit the binding between MITF and β-catenin in melanocytes, thereby inhibiting the melanin formation.

Figure 2:
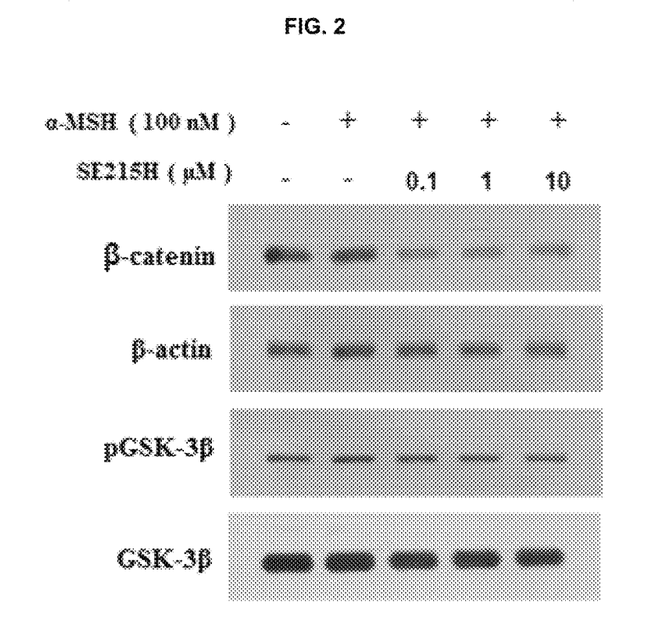
FIG. 2 shows the results obtained by evaluating the inhibitory effects of the peptide fragment of the present invention on expression and activation of the molecules associated with Wnt signaling pathways in human epidermal melanocytes.

Experimental Example 2: Evaluation of the Effects of the Peptide Fragment of the Present Invention on β-Catenin Expression and GSK-3 Phosphorylation in Human Epidermal Melanocytes The effects of the peptide fragment of the present invention on the β-catenin expression and the GSK-3 phosphorylation, which plays a critical role in the activation of Wnt signaling pathways, were evaluated using a Western blotting assay. Human epidermal melanocytes (Cascade Biologics, #C-0245C; Portland, Oreg., USA) were added to 2 ml of DMEM in each well of a 6-well microplate ($1.5 \times 10^5$ cells per well). The cells were then stabilized through incubating in a 5% $CO_2$ incubator at 37° C. for 24 hours. α-MSH (Sigma Co, MO, USA), a melanocyte-stimulating hormone, was treated to each well, along with the peptide fragment of the present invention (the peptide of SEQ ID NO: 8) in predetermined concentrations. After the cells were cultured for 48 hours, the proteins were extracted therefrom. The obtained extracts were subject to the Western blotting assay using an anti-β-catenin antibody (Santa Cruz Co., CA, USA) and an anti-pGSK-3 antibody (Cell SignalingTechnology, MA, USA), so as to measure the levels of β-catenin expression and GSK-3 phosphorylation changes. The results thereof are shown in FIG. 2. As shown in FIG. 2, the levels of β-catenin expression and GSK-3 phosphorylation were decreased by the peptide of SEQ ID NO: 8 in concentration-dependent manner. Therefore, it can be seen that the peptide fragments of the present invention can inhibit the Wnt signaling pathways in melanocytes.

Experimental Example 3: Tests for Inhibitory Activity Against Melanin Formation in the Mouse Melanoma Cell Line B16F10

B16F10 cells (Korean Cell Line Bank, Seoul) were added to each well of a 6-well microplate ($1.5 \times 10^5$ cells per well), along with 2 ml of DMEM, and then incubated in a 5% $CO_2$ incubator at 37° C. for 24 hours. α-MSH (Sigma Co, MO, USA) (100 nM) was treated to each well, along with the peptide of SEQ ID NO: 8 in the final concentrations of 0.1, 1, and 10 μM. The groups in which α-MSH (100 nM) and arbutin (0.01%) were respectively treated were used as positive controls. After additionally incubating the cells for 24 hours, the pictures of each culture ware taken so as to compare the respective levels of melanin formation.

Figure 3:
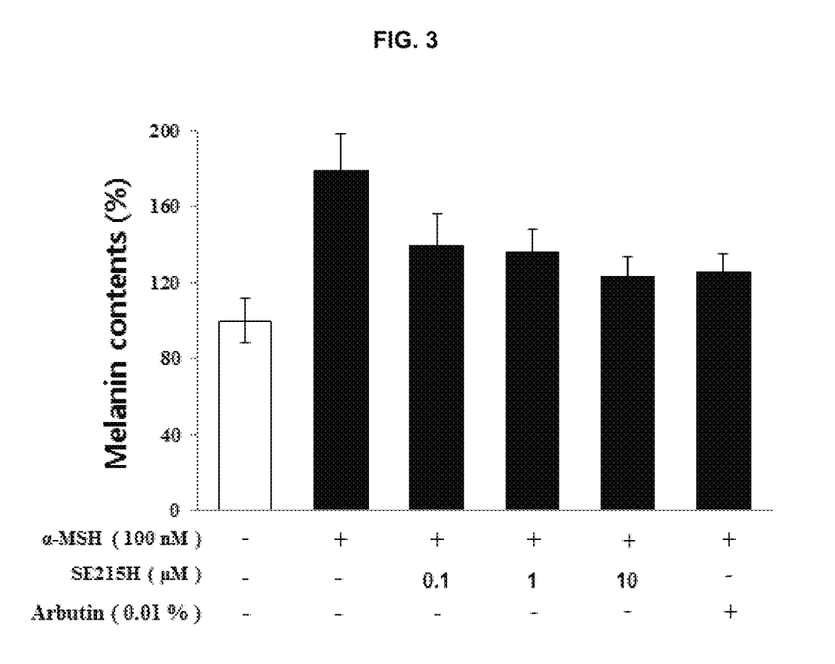
FIG. 3 shows the results obtained by evaluating the inhibitory activity of the peptide fragment of the present invention against the melanin formation in the mouse melanoma cell line.

As shown in FIG. 3, in the groups treated with the peptide of SEQ ID NO: 8, the brown colors of each cell culture were decreased according to the concentrations of the peptide, showing colors similar to the positive controls. These results show that the peptide fragments of the present invention inhibit α-MSH-stimulated melanin pigment formation in melanocytes.

Experimental Example 4: Tests for Inhibitory Activity Against Tyrosinase Activity in the Mouse Melanoma Cell Line B16F10

We evaluated whether the peptide fragment of the present invention inhibits tyrosinase activity. B16F10 cells (Korean Cell Line Bank, Seoul) were added to each well of a 24-well plate ($5 \times 10^4$ cells per well), along with 1 ml of DMEM, and then stabilized through incubating in a 5% $CO_2$ incubator at 37° C. for 24 hours. α-MSH (Sigma Co, MO, USA), a melanocyte-stimulating hormone, was treated to each well, along with the peptide of SEQ ID NO: 8 in predetermined concentrations. After incubating the cells for 72 hours, the proteins were extracted therefrom. The obtained extracts were added to each well of a 96-well plate (30 g per each well) and then treated with a L-dihydroxyphenylalanine (L-DOPA) solution (100 μL) at 37° C. for 2 hours. The groups in which α-MSH (100 nM) and arbutin (0.01%) were respectively treated were used as positive controls. After 2 hours, the pictures thereof were taken and the tyrosinase activities thereof were measured at 490 nm with a microreader.

Figure 4:
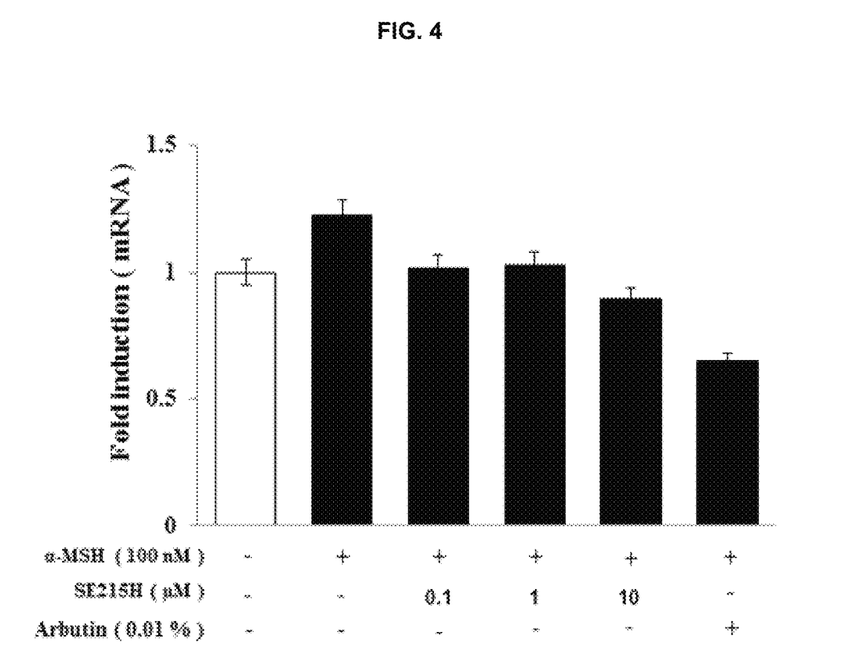
FIG. 4 shows the results obtained by evaluating the effects of the peptide fragment of the present invention on the tyrosinase activity in the mouse melanoma cell line.

As shown in FIG. 4, in the control group treated with only α-MSH, the tyrosinase activity thereof was increased. In contrast, in the test groups treated with both α-MSH and the peptide of SEQ ID NO: 8, the tyrosinase activities were decreased in concentration-dependent manner. These results show that the peptide fragments of the present invention have an inhibitory activity against tyrosinase activity.

Figure 5:
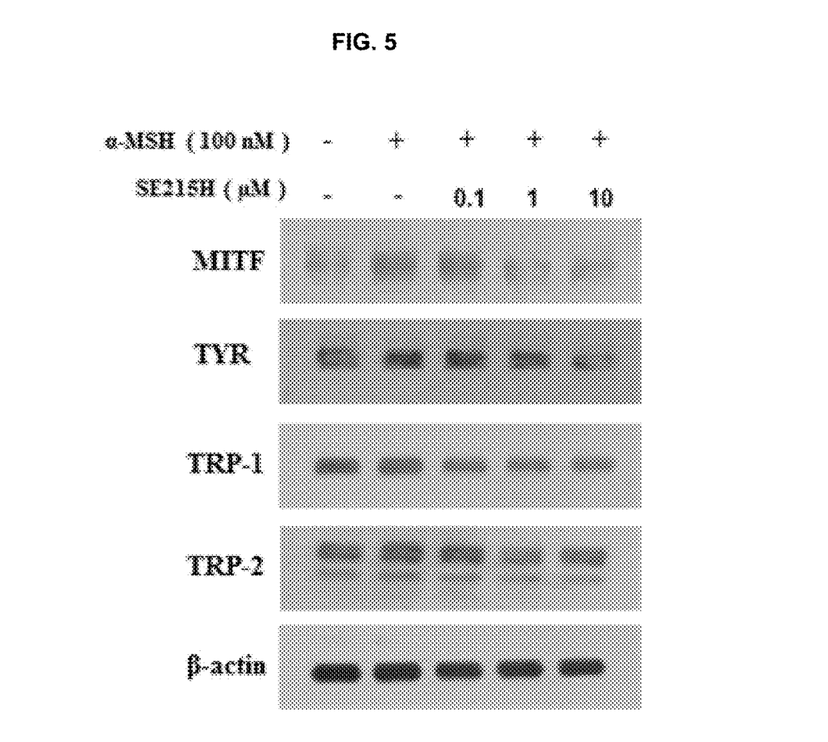
FIG. 5 shows the results obtained by evaluating the effects of the peptide fragment of the present invention on the expressions of melanin-producing enzymes in human epidermal melanocytes.

Experimental Example 5: Tests for Inhibitory Activity Against Protein Expressions of the Melanin-Producing Enzymes in Human Epidermal Melanocytes We evaluated the effects of the peptide fragment of the present invention on the protein expressions of the melanin-producing enzymes in human epidermal melanocytes, using a Western blotting assay. Human epidermal melanocytes (Cascade Biologics, #C-0245C; Portland, Oreg., USA) were added to each well of a 6-well microplate (1.5×10⁵ cells per well), along with 2 ml of DMEM, and then stabilized through incubating in a 5% $CO_2$ incubator at 37° C. for 24 hours. α-MSH (Sigma Co, MO, USA), a melanocyte-stimulating hormone, was treated to each well, along with the peptide fragment of the present invention (the peptide of SEQ ID NO: 8) in predetermined concentrations. After incubating the cells for 24 hours, the proteins were extracted therefrom. The obtained extracts were subject to the Western blotting assay using an anti-MITF antibody (ABcam, Ma, USA), an anti-tyrosinase antibody (Santa Cruz Co., CA, USA), an anti-TRP-1 antibody (Santa Cruz Co., CA, USA), and an anti-TRP-2 antibody (Santa Cruz Co., CA, USA), so as to measure the expression levels of MITF, tyrosinase, TRP-1, and TRP-2. The results thereof are shown in FIG. 5. As shown in FIG. 5, the expression levels of MITF, tyrosinase, TRP-1, and TRP-2 were decreased by the treatment of the peptide of SEQ ID NO: 8 in concentration-dependent manner. Therefore, it can be seen that the peptide fragments of the present invention inhibit the synthesis of MITF, tyrosinase, TRP-1, and TRP-2 in human epidermal melanocytes.

Experimental Example 6: Tests for Inhibitory Activity Against Gene Expressions of the Melanin-Producing Enzymes in Human Epidermal Melanocytes We evaluated whether the peptide fragment of the present invention inhibits gene expressions of the melanin-producing enzymes. Human epidermal melanocytes were added to each well of a 6-well plate (1.5×10⁵ cells per well), along with 2 ml of DMEM, and then stabilized through incubating in a 5% $CO_2$ incubator at 37° C. for 24 hours. α-MSH (Sigma Co, MO, USA), a melanocyte-stimulating hormone, was treated to each well, along with the peptide of SEQ ID NO: 8 in predetermined concentrations. After incubating the cells for 72 hours, the total RNAs were extracted therefrom and then cDNAs were synthesized. The cDNA syntheses were carried out with a Reverse Transcription Master premix (Elpisbiotech, Daejeon, Korea). Using each synthesized cDNA as a template, reverse transcription polymerase chain reactions (RT-PCR) were carried out with a ROTOR Q GENE apparatus. The primer sets for the RT-PCR were shown in the following table 2. Each RT-PCR solution was prepared by mixing 1 μl of cDNA, 10 μl of TOPreal qRT-PCR2X premix (Enzynomics, Daejeon, Korea), 2 μl of primer set (10 pmol) and 7 μl of D.W. The RT-PCR was carried out as follows: initially at 94° C. for 10 minutes; and then at 94° C. for 10 seconds, at 58° C. for 30 seconds, and at 72° C. for 1 minute; 40 cycles.

TABLE 2

|  | SEQ ID NO | | Sequence of Primer |
|---|---|---|---|
| MITF | 10 | Forward | CTCGAGCTCATGGACTTTCC |
|  | 11 | Reverse | CCAGTTCCGAGGTTGTTGTT |
| Tyrosinase | 12 | Forward | ATCCAGAAGCTGACAGG |
|  | 13 | Reverse | TTTGAGAGGCATCCGCTA |
| TRP-1 | 14 | Forward | AGCAGTAGTTGGCGCTTTGT |
|  | 15 | Reverse | TCAACCAGGTGGTTTTGTGA |
| TRP-2 | 16 | Forward | TGCCACAACATGGATGAACT |
|  | 17 | Reverse | TTGTGCCCACCAAACAGTAA |
| GAPDH | 18 | Forward | GCAAATTCCATGGCACCGT |
|  | 19 | Reverse | CCAAAATCAAGTGGGGCGA |

Figure 6:
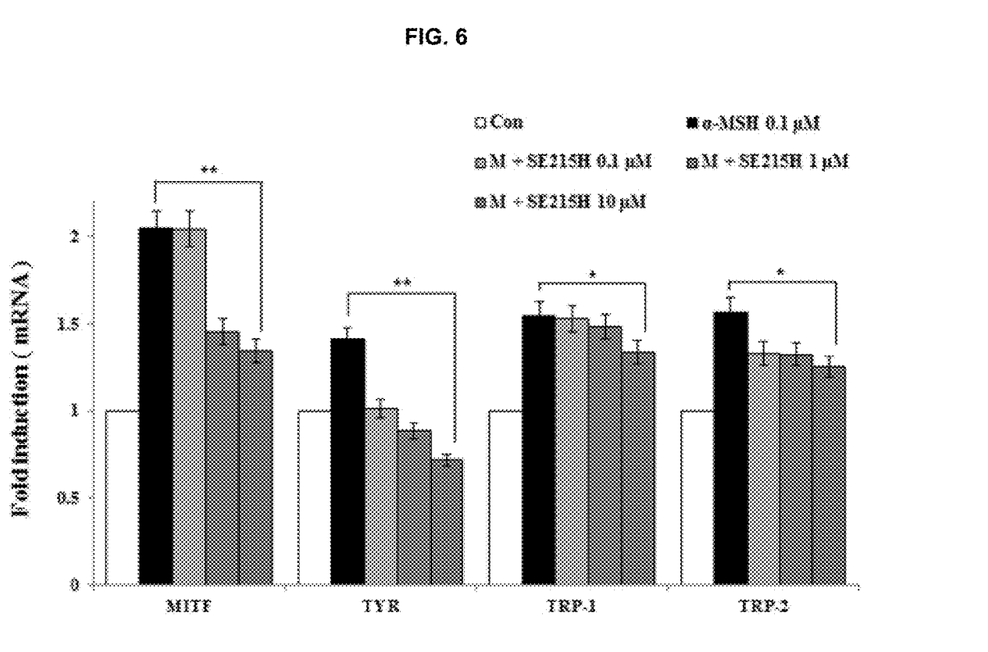
FIG. 6 shows the results obtained by evaluating the effects of the peptide fragment of the present invention on the gene expressions of melanin-producing enzymes in human epidermal melanocytes.

The results obtained by measuring the gene expressions of MITF, tyrosinase, TRP-1 and TRP-2 through the above RT-PCRs are shown in FIG. 6.

As shown in FIG. 6, the gene expressions of MITF, tyrosinase (TYR), TRP-1 and TRP-2 were increased in the control group treated with only α-MSH. In contrast, in the test groups treated with both α-MSH and the peptide fragment of the present invention (i.e., the peptide of SEQ ID NO: 8), the gene expressions of MITF, tyrosinase, TRP-1 and TRP-2 were decreased in concentration-dependent manner. These results show that the peptide fragments of the present invention inhibit the gene expressions of MITF, tyrosinase, TRP-1 and TRP-2.

The invention claimed is:

1. A peptide for inhibiting Wnt signaling pathways consisting of the amino acid sequence of SEQ ID NO: 1, 2, 3, 4, or 9.

2. A composition inhibiting Wnt signaling pathways, comprising the peptide of claim 1.

* * * * *